(12) United States Patent
Wadsworth et al.

(10) Patent No.: US 8,771,641 B2
(45) Date of Patent: Jul. 8, 2014

(54) ARYLOXYANILIDE IMAGING AGENTS (75) Inventors: Harry John Wadsworth, Amersham (GB); Dennis O'Shea, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 36 days.

(21) Appl. No.: 13/510,041

(22) PCT Filed: Dec. 16, 2010

(86) PCT No.: PCT/EP2010/069866
§ 371 (c)(1),
(2), (4) Date: May 16, 2012

(87) PCT Pub. No.: WO2011/073304
PCT Pub. Date: Jun. 23, 2011

(65) Prior Publication Data
US 2012/0244073 A1    Sep. 27, 2012

Related U.S. Application Data (60) Provisional application No. 61/287,233, filed on Dec. 17, 2009.

(30) Foreign Application Priority Data

Dec. 17, 2009  (GB) .................................. 0921967.6

(51) Int. Cl.
*A61K 51/04*    (2006.01)
*A61K 31/44*    (2006.01)

(52) U.S. Cl.
USPC .......... 424/1.89; 546/261; 546/265; 546/297; 546/300; 546/337

(58) Field of Classification Search
USPC ........ 424/1.89, 9.1, 9.341, 9.4; 546/261, 265, 546/297, 300, 337; 514/332, 335, 351, 352, 514/357

See application file for complete search history.

(56) References Cited

U.S. PATENT DOCUMENTS

2012/0003154 A1 *  1/2012  Wadsworth et al. ......... 424/1.89

FOREIGN PATENT DOCUMENTS

WO      2007/074883        7/2007

OTHER PUBLICATIONS

Imaizumi, et.al. Synapse 200708 vol. 61, No. 8, Aug. 2007 pp. 595-605.
Le Fur, et.al. Life Sciences, vol. 33, No. 5, 1983 pp. 449-457.
Briard, et.al. Journal of Medicinal Chemistry, vol. 52, No. 3, Feb. 12, 2009 pp. 688-699.
PCT/EP2010/069866 ISRWO Dated Apr. 8, 2011.
GB0929967.6 Search Report Dated Mar. 31, 2010.

* cited by examiner

*Primary Examiner* — Michael G Hartley
*Assistant Examiner* — Jagadishwar Samala (57) ABSTRACT

The present invention provides a novel radiolabeled aryloxyalinine derivative suitable for in vivo imaging. In comparison to known aryloxyalinine derivative in vivo imaging agents, the in vivo imaging agent of the present invention has better properties for in vivo imaging. The in vivo imaging agent of the present invention demonstrates good selective binding to the peripheral benzodiazepine receptor (PBR), in combination with good brain uptake and in vivo kinetics following administration to a subject.

9 Claims, 3 Drawing Sheets

ARYLOXYANILIDE IMAGING AGENTS

This application is a filing under 35 U.S.C. 371 of international application number PCT/EP2010/069866, filed Dec. 16, 2010, which claims priority to U.S. application No. 61/287,233 filed Dec. 17, 2009 and Great Britain application number 0921967.6 filed Dec. 17, 2009, the entire disclosure of which is hereby incorporated by reference.

TECHNICAL FIELD OF THE INVENTION

The present invention concerns in vivo imaging and in particular in vivo imaging of peripheral benzodiazepine receptors (PBR). An aryloxyanilide in vivo imaging agent is provided that binds with nanomolar affinity to PBR, has good uptake into the brain following administration, and which has good selective binding to PBR. The present invention also provides a precursor compound useful in the synthesis of the in vivo imaging agent of the invention, as well as a method for synthesis of said in vivo imaging agent comprising use of said precursor compound, and a kit for carrying out said method. A cassette for the automated synthesis of the in vivo imaging agent is also provided. In addition, the invention provides a radiopharmaceutical composition comprising the in vivo imaging agent of the invention, as well as methods for the use of said in vivo imaging agent.

DESCRIPTION OF RELATED ART

The peripheral benzodiazepine receptor (PBR) is known to be mainly localised in peripheral tissues and glial cells but its physiological function remains to be clearly elucidated. Subcellularly, PBR is known to localise on the outer mitochondrial membrane, indicating a potential role in the modulation of mitochondrial function and in the immune system. It has furthermore been postulated that PBR is involved in cell proliferation, steroidogenesis, calcium flow and cellular respiration. PBR has been associated with a variety of conditions including acute and chronic stress, anxiety, depression, Parkinson's disease, Alzheimer's disease, brain damage, cancer (Gavish et al Pharm Rev 1999; 51: 629), Huntington's disease (Meβmer and Reynolds Neurosci Lett 1998; 241: 53-6), asthma (Pelaia et al Gen Pharmacol 1997; 28(4): 495-8), rheumatoid arthritis (Bribes et al Eur J Pharmacol 2002; 452(1): 111-22), atherosclerosis (Davies et al J Nucl Med 2004; 45: 1898-1907) and multiple sclerosis (Banati et al Brain 2000; 123: 2321). PBR may also be associated with neuropathic pain, Tsuda et al having observed activated microglia in subjects with neuropathic pain (TINS 2005; 28(2): 101-7).

Positron emission tomography (PET) imaging using the PBR selective ligand, (R)-[$^{11}$C]PK11195 provides a generic indicator of central nervous system (CNS) inflammation. Despite the successful use of (R)-[$^{11}$C]PK11195, it has its limitations. It is known to have high protein binding, and low specific to non-specific binding. The role of its radiolabelled metabolites is not known and quantification of binding requires complex modelling. There have been efforts to provide compounds having high affinity and selectivity for PBR to enable improved measurement of PBR in the CNS.

Aryloxyalinine derivatives have been proposed that have high affinity for PBR, as well as high selectivity for PBR over the central benzodiazepine receptor (CBR) (Chaki et al Eur J Pharmacol 1999; 371: 197-204). [$^{11}$C]-DAA1106 and [$^{18}$F]-FE-DAA1106 are PET radioligands based on these aryloxyalinine compounds. These PET radioligands are taught in U.S. Pat. No. 6,870,069, and have been studied in humans (Ikomo et al J Cereb Blood Flow Metab 2007; 27: 173-84 and Fujimura et al J Nuc Med 2006; 47: 43-50). Alternative radiofluorinated DAA1106 derivatives are taught in WO 2007/074383. Alternative $^{11}$C-labelled DAA1106 derivatives are described in WO 2007/036785. Radioiodinated DAA1106 is described in EP 1854781, and by Zhang et al (J Med Chem 2007; 50: 848-55). The chemical structures of [$^{11}$C]-DAA1106, [$^{18}$F]-FE-DAA1106 and [$^{123}$I]-DAA1106 are as follows:

[$^{11}$C]-DAA1106

[$^{18}$F]-FE-DAA1106

[$^{131}$I]-DAA1106

However, the kinetic properties of these compounds are not ideal for in vivo imaging such that their application to quantitative studies are believed to be limited.

More recently, a compound known as PBR06 has been reported as having improved properties for in vivo imaging as compared with the above-described compounds. The structure of this compound is as follows:

PBR06

Although metabolised quite rapidly in the periphery, the metabolites of PBR06 do not penetrate the blood-brain barrier (Briard et al J Med Chem 2009; 52: 688-699). In contrast to the earlier compounds, almost the entire signal coming from the brain is from intact PBR06. This enables the concentration of PBR in the brain to be accurately determined. PBR06 is therefore regarded as a promising in vivo imaging agent.

However, and as presented in the present specification, the ratio of uptake of PBR06 in tissues that have a relatively high expression of PBR (i.e. olfactory bulb) as compared with background tissues (i.e. striatum) is less than optimal for in vivo imaging. There is also scope to improve the proportion of intact compound in the brain.

There is therefore a need for alternative in vivo imaging agents having improved properties for in vivo imaging as compared with PBR06, i.e. higher specific uptake in PBR-expressing tissues, and/or higher proportion of intact compound in the brain.

SUMMARY OF THE INVENTION

The present invention provides a novel radiolabelled aryloxyalinine derivative suitable for in vivo imaging. In comparison to known aryloxyalinine derivative in vivo imaging agents, the in vivo imaging agent of the present invention has better properties for in vivo imaging. The in vivo imaging agent of the present invention demonstrates improved specific binding to the peripheral benzodiazepine receptor (PBR), in addition to having good brain uptake and favourable in vivo kinetics.

DETAILED DESCRIPTION OF THE INVENTION

Imaging Agent

In one aspect, the present invention provides an in vivo imaging agent of Formula I:

wherein:
$A^1$ is —$CR^1R^2$—$(CH_2)_n$— wherein $R^1$ and $R^2$ are independently selected from hydrogen, fluoro, or $C_{1-3}$ alkyl, and n is 0, 1 or 2;

$A^2$ is —$CH_2$—, —O— or —O—$CH_2$—; or,

-$A^1$-$A^2$- is —CH=CH—.

An "in vivo imaging agent" in the context of the present invention is a radiolabelled compound suitable for in vivo imaging. The term "in vivo imaging" as used herein refers to those techniques that non-invasively produce images of all or part of the internal aspect of a subject. Examples of such in vivo imaging methods are single photon emission computed tomography (SPECT) and positron emission tomography (PET).

Unless otherwise specified, the term "alkyl" alone or in combination, means a straight-chain or branched-chain alkyl radical containing preferably from 1 to 3 carbon atoms. Examples of such radicals include, methyl, ethyl, and propyl.

Examples of some in vivo imaging agents of the invention are as follows:

1

(8)

(II)

wherein $A^1$ and $A^2$ are as suitably and preferably defined herein for the in vivo imaging agent of Formula I, and LG is a leaving group.

A "precursor compound" comprises a non-radioactive derivative of the in vivo imaging agent, designed so that chemical reaction with a convenient chemical form of $^{18}F$ occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

The term "a suitable source of $^{18}F$" means $^{18}F$ in a chemical form that is reactive with a substituent of the precursor compound such that $^{18}F$ becomes covalently attached thereby forming the desired in vivo imaging agent.

Broadly speaking, the step of "reacting" the precursor compound with said suitable source of $^{18}F$ involves bringing the two reactants together under reaction conditions suitable for formation of the desired in vivo imaging agent in as high a radiochemical yield (RCY) as possible. Some more detailed routes are presented in the experimental section below.

The term "leaving group" refers to an atom or group of atoms that leaves a molecule with a pair of electrons in heterolytic bond cleavage, usually to be replaced by a nucleophile. A leaving group can be an anion or a neutral molecule. Preferred leaving groups (LG) are mentioned below.

Okubu et al (2004 Bioorg. Med. Chem.; 12: 423-38) describe methods to obtain non-radioactive aryloxyanilide compounds. Synthetic schemes to obtain aryloxyanilide compounds are also described by Briard et al (J. Med. Chem. 2008; 51; 17-31), Wilson et al (Nuc. Med. Biol. 2008; 35; 305-14), and Zhang et al (J. Med. Chem. 2007; 50: 848-55). These prior art methods can be easily adapted to obtain a precursor compound of Formula II.

Scheme I below is a generic reaction scheme to obtain non-radioactive standards, and precursor compounds suitable for preparation of the in vivo imaging agents of the present invention:

$A^1$ of Formula I is preferably —$CR^1R^2$—$(CH_2)_n$—, most preferably —$(CH_2)_n$— wherein m is 1, 2 or 3, and especially preferably 1 or 2. $A^2$ of Formula I is preferably —$CH_2$— or —O—. Especially preferably -$A^1$-$A^2$- is selected from —$CH_2$—$CH_2$—, —$CH_2$—O— and —$CH_2$—$CH_2$—O—. Preferred in vivo imaging agents of the invention are in vivo imaging agents 1-4, most preferably in vivo imaging agents 1-3, especially preferably in vivo imaging agents 1 and 2 and most especially preferably in vivo imaging agent 1.

Example 11 describes the rat biodistribution model that was used to compare in vivo imaging agents of the invention with PBR06. Evaluation of the OB:striatum uptake as compared with PBR06 revealed that in vivo imaging agent 1 was taken up relatively more in the OB as compared with the striatum (see FIG. 1 herein), and in vivo imaging agents 2 and 3 were comparable with PBR06 (see FIGS. 2 and 3). As OB is known to express higher levels of PBR compared with other areas of rat brain (see "Handbook of Substance Abuse" by Tarter, Ammerman and Ott; Springer 1998: 398-99) the ratio OB:striatum is a measure of specificity of test compound uptake.

Example 12 describes the assay used to evaluate the amount of intact test in vivo imaging agent in rat brain at 60 minutes post-injection. In vivo imaging agents 1-4 demonstrated the same favourable metabolism profile as PBR06, i.e. a high proportion of radioactivity in the brain at 60 minutes post-injection was found to be intact test compound. In vivo imaging agents 1 and 2 were found to have an even higher proportion intact in the brain at 60 minutes post-injection as compared with PBR06.

In vivo imaging agents of the present invention are shown herein to have superior properties for in vivo imaging of PBR as compared with known such agents.

Method for Preparation

In a further aspect, the present invention provides a method for the preparation of the in vivo imaging agent as defined herein, wherein said method comprises reacting a suitable source of $^{18}F$ with a precursor compound of Formula II:

Scheme 1

In the above reaction scheme, LG is a leaving group as defined herein, and R* represents the fused bicyclic ring structure that includes the A ring, as comprised in both Formula I and Formula II above. Reduction of the nitro group in commercially-available 2-nitrobiphenyl ether (a) by hydrogenation gives the corresponding aniline (b). Reductive alkylation with an aromatic aldehyde (c) gives the benzylamine (d). Reaction with the appropriate acetyl (e) results in the desired non-radioactive standard or precursor compound.

Labelling with $^{18}$F is achieved by nucleophilic displacement of the leaving group LG from the precursor compound of Formula II. Preferred leaving groups (LG) include chloride, bromide, iodide, tosylate, mesylate, and triflate, with bromide and tosylate being most preferred. The precursor compound of Formula II may be labelled in a one step reaction wherein the suitable source of $^{18}$F is [$^{18}$F]-fluoride. [$^{18}$F] fluoride ($^{18}$F$^{-}$) for radiofluorination reactions is normally obtained as an aqueous solution from the nuclear reaction $^{18}$O(p,n)$^{18}$F and is made reactive by the addition of a cationic counterion and the subsequent removal of water. Suitable cationic counterions should possess sufficient solubility within the anhydrous reaction solvent to maintain the solubility of $^{18}$F$^{-}$. Therefore, counterions that have been used include large but soft metal ions such as rubidium or caesium, potassium complexed with a cryptand such as Kryptofix™, or tetraalkylammonium salts. A preferred counterion is potassium complexed with a cryptand such as Kryptofix™ because of its good solubility in anhydrous solvents and enhanced $^{18}$F$^{-}$ reactivity.

To ensure that radiofluorination takes place at a particular site, the precursor compound may need to be selectively chemically protected. Protecting groups have been discussed above.

The precursor compound is ideally provided in sterile, apyrogenic form. It can accordingly be used for the preparation of a pharmaceutical composition comprising the in vivo imaging agent together with a biocompatible carrier suitable for mammalian administration. The precursor compound is also suitable for inclusion as a component in a kit for the preparation of such a pharmaceutical composition.

In a preferred embodiment, the precursor compound is provided in solution and as part of a kit, or of a cassette designed for use in an automated synthesis apparatus. These aspects are discussed in more detail below in relation to additional aspects of the invention.

In another preferred embodiment, the precursor compound is bound to a solid phase. The precursor compound is preferably supplied covalently attached to a solid support matrix. In this way, the desired product forms in solution, whereas starting materials and impurities remain bound to the solid phase. As an example of such a system, precursor compounds for solid phase electrophilic fluorination with $^{18}$F-fluoride are described in WO 03/002489, and precursor compounds for solid phase nucleophilic fluorination with $^{18}$F-fluoride are described in WO 03/002157.

Preferably, the method of the present invention is automated for ease of performance.

Precursor Compound

The precursor compound as suitably and preferably described above in relation to the method of the invention itself forms an additional aspect of the present invention.

Radiopharmaceutical Composition

In a yet further aspect, the present invention provides a "radiopharmaceutical composition", which is a composition comprising the in vivo imaging agent of the invention, together with a biocompatible carrier in a form suitable for mammalian administration.

The "biocompatible carrier" is a fluid, especially a liquid, in which the in vivo imaging agent is suspended or dissolved, such that the radiopharmaceutical composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

Suitable and preferred embodiments of the in vivo imaging agent when comprised in the radiopharmaceutical composition of the invention are as defined above. The radiopharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). Where the in vivo imaging agent of the invention is provided as a radiopharmaceutical composition, the method for preparation of said in vivo imaging agent may further comprise the steps required to obtain a radiopharmaceutical composition, e.g. removal of organic solvent, addition of a biocompatible buffer and any optional further ingredients. For parenteral administration, steps to ensure that the radiopharmaceutical composition is sterile and apyrogenic also need to be taken.

Kit and Cassette

In a preferred embodiment, the method for the preparation of the in vivo imaging agent of the invention is carried out by means of a kit, or using a cassette that can plug into an automated synthesiser. These kits and cassettes in turn form further aspects of the invention, and are particularly convenient for the preparation of the radiopharmaceutical composition of the invention as defined herein.

The kit of the invention comprises the precursor compound of the invention in a sealed container. The "sealed container" preferably permits maintenance of sterile integrity and/or radioactive safety, plus optionally an inert headspace gas (e.g. nitrogen or argon), whilst permitting addition and withdrawal of solutions by syringe. A preferred sealed container is a septum-sealed vial, wherein the gas-tight closure is crimped on with an overseal (typically of aluminium). Such sealed containers have the additional advantage that the closure can withstand vacuum if desired e.g. to change the headspace gas or degas solutions.

Suitable and preferred embodiments of the precursor compound when employed in the kit of the invention are as already described herein.

The precursor compound for use in the kit may be employed under aseptic manufacture conditions to give the desired sterile, non-pyrogenic material. The precursor compound may alternatively be employed under non-sterile conditions, followed by terminal sterilisation using e.g. gamma-irradiation, autoclaving, dry heat or chemical treatment (e.g. with ethylene oxide). Preferably, the precursor compound is provided in sterile, non-pyrogenic form. Most preferably the sterile, non-pyrogenic precursor compound is provided in the sealed container as described above.

Preferably, all components of the kit are disposable to minimise the possibilities of contamination between runs and to ensure sterility and quality assurance.

In another aspect, the present invention provides a cassette which can be plugged into a suitably adapted automated synthesiser for the synthesis of the in vivo imaging agent of the invention. [$^{18}$F]-radiotracers in particular are now often conveniently prepared on an automated radiosynthesis apparatus. There are several commercially-available examples of such apparatus, including Tracerlab™ and Fastlab™ (both available from GE Healthcare). The radiochemistry is performed on the automated synthesis apparatus by fitting the cassette to the apparatus. The cassette normally includes fluid pathways, a reaction vessel, and ports for receiving reagent vials as well as any solid-phase extraction cartridges used in post-radiosynthetic clean up steps.

The cassette for the automated synthesis of the in vivo imaging agent of the invention comprises:

(i) a vessel containing a precursor compound as defined herein; and
(ii) means for eluting the vessel with a suitable source of $^{18}$F, as defined herein.

The cassette may additionally comprise:

(iii) an ion-exchange cartridge for removal of excess $^{18}$F; and optionally,
(iv) a cartridge for deprotection of the resultant radiolabelled product to form an in vivo imaging agent as defined herein.

The reagents, solvents and other consumables required for the automated synthesis may also be included together with a data medium, such as a compact disc carrying software, which allows the automated synthesiser to be operated in a way to meet the end user's requirements for concentration, volumes, time of delivery etc.

Methods of Use

In a yet further aspect, the present invention provides an in vivo imaging method for determining the distribution and/or the extent of PBR expression in a subject comprising:

(i) administering to said subject an in vivo imaging agent as defined herein;
(ii) allowing said in vivo imaging agent to bind to PBR in said subject;
(iii) detecting by an in vivo imaging procedure signals emitted by $^{18}$F of said in vivo imaging agent;
(iv) generating an image representative of the location and/or amount of said signals; and,
(v) determining the distribution and extent of PBR expression in said subject wherein said expression is directly correlated with said signals emitted by said $^{18}$F.

For the in vivo imaging method of the invention, suitable and preferred aspects of the in vivo imaging agent are as defined earlier in the specification.

"Administering" the in vivo imaging agent is preferably carried out parenterally, and most preferably intravenously. The intravenous route represents the most efficient way to deliver the in vivo imaging agent throughout the body of the subject, and therefore also across the blood-brain barrier (BBB) and into contact with PBR expressed in said subject. The in vivo imaging agent of the invention is preferably administered as the pharmaceutical composition of the invention, as defined herein. In an alternative embodiment, the administration step can be understood as a preliminary step carried out before the in vivo imaging method itself, such that step (i) can be defined as providing a subject to whom the in vivo imaging agent has been pre-administered.

Following the administering step and preceding the detecting step, the in vivo imaging agent is allowed to bind to PBR. For example, when the subject is an intact mammal, the in vivo imaging agent will dynamically move through the mammal's body, coming into contact with various tissues therein. Once the in vivo imaging agent comes into contact with PBR, a specific interaction takes place such that clearance of the in vivo imaging agent from tissue with PBR takes longer than from tissue without, or with less PBR. A certain point in time will be reached when detection of in vivo imaging agent specifically bound to PBR is enabled as a result of the ratio between in vivo imaging agent bound to tissue with PBR versus that bound in tissue without, or with less PBR. Ideally, this ratio is 2:1 or greater.

The "detecting" step of the method of the invention involves detection of signals emitted by the $^{18}F$ by means of a positron-emission tomography (PET) detector. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by said $^{18}F$. The signals emitted directly correlate with the expression of PBR such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study PBR in healthy subjects, or in subjects known or suspected to have a pathological condition associated with abnormal expression of PBR (a "PBR condition"). The in vivo imaging agents of the invention are particularly suited to in vivo imaging PBR expression in the central nervous system (CNS).

In an alternative embodiment, the in vivo imaging method of the invention may be carried out repeatedly during the course of a treatment regimen for said subject, said regimen comprising administration of a drug to combat a PBR condition. For example, the in vivo imaging method of the invention can be carried out before, during and after treatment with a drug to combat a PBR condition. In this way, the effect of said treatment can be monitored over time. PET imaging is particularly suitable for this embodiment. PET has excellent sensitivity and resolution, so that even relatively small changes in a lesion can be observed over time, which is advantageous for treatment monitoring. PET scanners routinely measure radioactivity concentrations in the picomolar range. Micro-PET scanners now approach a spatial resolution of about 1 mm, and clinical scanners about 4-5 mm.

Preferably, said method relates to the in vivo imaging of a subject known or suspected to have a PBR condition, and therefore is useful as part of a method for the diagnosis of said condition. The in vivo imaging method of the invention may therefore comprise the further step (vi) of attributing the distribution and extent of PBR expression to diagnose whether said subject is suffering from a PBR condition. Examples of such PBR conditions where in vivo imaging would be of use include neuropathologies such as Parkinson's disease, multiple sclerosis, Alzheimer's disease and Huntington's disease where neuroinflammation is present. Other PBR conditions that may be usefully imaged with the compounds of the invention include neuropathic pain, arthritis, asthma, atherosclerosis, a range of malignant diseases including but not limited to colorectal cancer and breast cancer, and also a range of mood disorders including but not limited to bipolar disorder, schizophrenia, anxiety and post-traumatic stress disorder.

In another aspect, the present invention provides the in vivo imaging agent as defined herein for use in the in vivo imaging method as suitably and preferably defined herein.

In a yet further aspect, the present invention provides the in vivo imaging agent as defined herein for the manufacture of a radiopharmaceutical composition as defined herein for use in the in vivo imaging method as suitably and preferably defined herein.

The invention is now illustrated by a series of non-limiting examples.

Brief Description of the Examples

Example 1 describes the synthesis of the direct labelling precursor for in vivo imaging agent 1.

Example 2 describes the synthesis of the direct labelling precursor for in vivo imaging agent 2.

Example 3 describes the synthesis of the direct labelling precursor for in vivo imaging agent 3.

Example 4 describes the synthesis of the direct labelling precursor for in vivo imaging agent 4.

Example 5 describes the radiofluorination method used to obtain in vivo imaging agents 1-4.

Example 6 describes the synthesis of a non-radioactive standard for in vivo imaging agent 1.

Example 7 describes the synthesis of a non-radioactive standard for in vivo imaging agent 2.

Example 8 describes the synthesis of a non-radioactive standard for in vivo imaging agent 3.

Example 9 describes the synthesis of a non-radioactive standard for in vivo imaging agent 4.

Example 10 describes the in vitro assay used to evaluate the affinity of non-radioactive standards of the imaging agents of the invention for PBR.

Example 11 describes the animal model used to determine biodistribution of the imaging agents of the invention following intravenous administration.

Example 12 describes the assay used to evaluate the metabolism of the imaging agents of the invention following intravenous administration.

LIST OF ABBREVIATIONS USED IN THE EXAMPLES

° C. degrees celsius
aq aqueous
BGO Bismuth germanate
DCM dichloromethane
DMF dimethyl formamide
DMSO dimethyl sulfoxide
EtOAc ethyl acetate
g grams
h hours
$K_i$ concentration of a compound required for half maximum inhibition
MBq megabequerels
mg milligrams
min minutes
ml milliliters
mM millimolar
mmol millimoles
n number of experiments
NMR nuclear magnetic resonance
PBR peripheral benzodiazepine receptor
rpm revolutions per minute
TEA triethylamine TLC thin layer chromatography
Tris tris(hydroxymethyl)aminomethane
UV ultraviolet

EXAMPLES

Example 1

Synthesis of the Direct Labelling Precursor for In Vivo Imaging Agent 1

Example 1(i)

2-Aminodiphenyl ether

2-Nitrodiphenyl ether (16 g, 74 mmol) in methanol (250 ml) was shaken with palladium on charcoal (1.6 g) under an atmosphere of hydrogen at 20-50° C. for 30 min. There was a rapid uptake of hydrogen and a detectable exotherm 20-50° C. with the temperature rapidly rising before cooling. Shaking was stopped for short periods to control the temperature from rising above 50° C. The reaction was then filtered through celite and concentrated in high vacuum to give 2-aminodiphenyl ether as an oil (13.5 g, 72.9 mmole, 98%) that crystallized on standing to give a buff solid.

$^1$H NMR (CDCl$_3$) 300 MHz δ 3.82 (2H, brm, NH$_2$), 6.7-7.1 (7H, m, ArH) 7.33 (2H, m, ArH).

$^{13}$C NMR (CDCl$_3$) 75 MHz δ 116.41, 117.03, 118.70 (2C), 120.22, 122.57, 124.85, 129.65 (2C), 138.70, 142.97, 157.43.

Example 1(ii)

N-(2,3-Dihydro-benzofuran-7-ylmethyl)-N-(2-phenoxyphenyl)-amine

2-Aminodiphenyl ether (1 g, 5.4 mmol) was treated with 2,3-Dihydro-benzofuran-7-carbaldehyde (1 g, 7.02 mmol) and toluene (10 ml) and heated at reflux for 4 h under an atmosphere of nitrogen with vigorous stirring. The solution became yellow and homogeneous. The reaction was then concentrated in vacuum to remove the toluene, cooled to 0° C., diluted with methanol (15 ml), and treated with sodium borohydride (612 mg 16 mmol) in portions over a period of 20 min. The reaction was then allowed to warm to room temperature and stirred for a further 30 min. 2N hydrochloric acid (5 ml) was added and the reaction stirred for a further 30 min. The reaction was then concentrated in vacuum to a gum and 10% aq potassium carbonate (50 ml) added. The product was then recovered by extraction into ethyl acetate (50 ml), the extract was dried over magnesium sulphate and concentrated in vacuum to a gum. The gum was chromatographed on a 120 g silica column in a gradient of 10-30% ethyl acetate in petrol. The main fast running fraction, N-(2,3-Dihydro-benzofuran-7-ylmethyl)-N-(2-phenoxyphenyl)-amine was collected as a gum (1.2824 g, 4.04 mmole, 74.9%) that crystallized on standing.

$^1$H NMR CDCl$_3$ 300 MHz, δ 3.19 (2H, t, CH$_2$Ph), 4.35 (2H, s, CH$_2$N) 4.51 (2H, t, CH$_2$O) 4.87 (1H, brs, NH), 6.6, –7.31 (12H, m ArH).

$^{13}$C NMR CDCl$_3$, 75 MHz δ 29.69, 42.63, 71.11, 112.01, 116.82, 117.27, 119.34, 120.31, 122.48, 123.64, 126.96, 129.55, 140.50, 143.07, 157.71, 157.83.

Example 1(iii)

2-Bromo-N-(2,3-dihydrofuran-7-ylmethyl)-N-(2-phenoxyphenyl)-acetamide

N-(2,3-Dihydrobenzofuran-7-ylmethyl)-N-(2-phenoxyphenyl)amine (0.5 g, 1.57 mmol) in dichloromethane (10 ml) was cooled to 0° C. and treated with bromoacetyl chloride (272 mg, 1.73 mmol) and triethylamine (175 mg, 1.73 mmol) and stirred for 1 h under an atmosphere of nitrogen. The reaction was diluted with dichloromethane (50 ml) and washed with 5N hydrochloric acid (20 ml) to remove the triethylamine and aqueous potassium carbonate (20 ml) to remove excess bromoacetyl chloride. The organic layer was separated, dried over magnesium sulphate and concentrated in high vacuum to give 2-bromo-N-(2,3-dihydrofuran-7-ylmethyl)-N-(2-phenoxyphenyl)acetamide. (661 mg, 1.51 mmole, 96%).

$^1$H NMR (CDCl$_3$) 300 MHz, δ3.06 (2H, m, CH$_2$Ph), 3.8 (2H, d, d CH$_2$O), 4.2-4.4 (2H, d, q, CH$_2$Br) 4.7, (1H, d, CHN), 5.12, (1H, d, CHN), 6.62-7.32 (12H, m, ArH).

$^{13}$C NMR (CDCl$_3$) 75 MHz δ 27.81, 29.68, 46.78, 70.89, 118.04, 119.36, 120.26, 123.06, 124.13, 124.17, 129.82, 153.48, 155.59, 158.55, 166.64.

Example 2

Synthesis of the Direct Labelling Precursor for In Vivo Imaging Agent 2

Example 2(i)

N-(benzo[1,3]dioxol-4-ylmethyl)-N-(2-phenyloxy-phenyl)amine

A mixture of 2-phenoxy-phenylamine (410 mg, 2.22 mmol) and 2,3-(methylenedioxy)-benzaldehyde (500 mg, 3.33 mmol) was heated at 90° C. for 2 h under nitrogen. The reaction was cooled to 0° C. and MeOH (4 mL) was added, followed by NaBH$_4$ (253 mg, 6.70 mmol) in portions over 20 min. The mixture was stirred at room temperature for 24 h. Formic acid (0.4 mL was added and the mixture stirred for 15 min. The solvents were removed in vacuo, the residue quenched with saturated aqueous NaHCO$_3$ (50 mL), extracted with DCM (2×30 mL), dried over MgSO$_4$, filtered and solvents removed in vacuo. The crude material was purified by silica gel chromatography eluting with petroleum spirit (A) and ethyl acetate (B) (5% B, 80 g, 4.0 CV, 60 mL/min) to afford 360 mg (51%) of N-(benzo[1,3]dioxol-4-ylmethyl)-N-(2-phenyloxy-phenyl) amine as a white solid.

$^1$H NMR (300 MHz, CDCl$_3$) δ 4.35 (2H, d, J=5.2 Hz, ArCH$_2$), 4.66 (1H, s, NH), 5.88 (2H, s, OCH$_2$O), 6.60-7.10 (10H, m, ArH), 7.24-7.34 (2H, m, ArH).

Example 2(ii)

N-(benzo[1,3]-dioxol-4-ylmethyl)-2-Bromo-N-(2-phenyloxy-phenyl)acetamide

To a solution of N-(benzo[1,3]dioxol-4-ylmethyl)-N-(2-phenyloxy-phenyl)amine (0.18 g, 0.58 mmol) dissolved in DCM (4 mL) was added triethylamine (0.24 g, 2.32 mmol, 0.32 mL). The reaction was cooled to 0° C. and bromoacetyl chloride (0.18 g, 1.16 mmol, 0.10 mL) was added. The mixture was stirred at room temperature for 2 h. LC-MS indicated starting material and product (1:1). Further triethylamine (0.24 g, 2.32 mmol, 0.32 mL) and bromoacetyl chloride (0.18 g, 1.16 mmol, 0.10 mL) were added and stirred at room temperature for 2 h. The solvents were removed in vacuo, the residue quenched with water (10 mL), extracted with DCM (2×20 mL), dried over MgSO$_4$, filtered and solvents removed in vacuo. The crude material was purified by silica gel chromatography eluting with DCM (A) and MeOH (B) (1% B, 80 g, 2 CV, 60 mL/min). The impure product was further purified by silica gel chromatography eluting with DCM (A) and EtOAc (B) (1-5% B, 80 g, 4.5 CV, 60 mL/min) to afford 120 mg (47%) of N-(benzo[1,3]dioxol-4-ylmethyl)-2-Bromo-N-(2-phenyloxy-phenyl)acetamide as a colourless oil.

$^1$H NMR (300 MHz, CDCl$_3$) δ 3.76 (1H, d, J=11 Hz, BrCH), 3.82 (1H, d, J=11 Hz, BrCH), 4.72 (1H, d, J=14 Hz, ArCH), 5.13 (1H, d, J=14 Hz, ArCH), 5.63 (1H, d, J=1 Hz, OCHO), 5.79 (1H, d, J=1 Hz, OCHO), 6.65-7.40 (12H, m, ArH).

LC-MS: m/z calcd for C$_{22}$H$_{18}$BrNO$_4$ 440.3. found, 441.9 (M+H)+.

Example 3

Synthesis of the Direct Labelling Precursor for In Vivo Imaging Agent 3

Example 3(i)

N-(2,3-Dihydrobenzo[1,4]dioxinyl-5-ylmethyl)-N-(2-phenoxyphenyl)-amine

2-Aminodiphenyl ether (1 g, 5.4 mmol) was treated with 2,3-Dihydro-benzo[1,4]dioxinyl-5-aldehyde. (885 mg, 5.4 mmol) and toluene (10 ml) and heated at reflux for 4 h under an atmosphere of nitrogen with vigorous stirring. The solution became yellow and homogeneous. The reaction was then concentrated in vacuum to remove the toluene, cooled to 0° C., and diluted with methanol (25 ml) and treated with sodium borohydride (1 g, pellet) with continuous stirring. The reaction was then allowed to warm to room temperature overnight when a white crystalline solid had precipitated. The solid collected by filtration was (N-(2,3-Dihydrobenzo-[1,4]dioxinyl-5-ylmethyl)-N-(2-phenoxyphenyl)-amine, 1.128 g, 3.56 mmole, 66%.

$^1$H NMR CDCl$_3$ 300 MHz, δ 4.16, (4H, s, CH$_2$—O×2), 4.35 (2H, d, CH$_2$N), 4.68 (1H, t, NH), 6.6-7.1 (10H, m ArH), 7.29, (2H, t, ArH).

$^{13}$C NMR CDCl$_3$, 75 MHz, δ42.6, 64.06, 64.21, 112.18, 116.25, 117.09, 119.57, 120.62, 120.79, 124.97, 128.00, 129.58, 140.55, 141.00, 142.97, 143.33, 157.78.

Example 3(ii)

N-(2,3-Dihydro-benzo-[1,4]dioxinyl-5-ylmethyl)-2-bromo-N-(2-phenoxyphenyl)acetamide N-(2,3-Dihydro-benzo[1,4]dioxin-5-ylmethyl)-N-(2-phenoxyphenyl)-amine (pure)(0.5 g, 1.5 mmol) in dichloromethane (20 ml) was treated with bromoacetyl chloride (259 mg, 1.65 mmol) and triethylamine (168 mg, 1.65 mmol) at 0° C. for 1 h. The reaction was then diluted with dichloromethane (50 ml) and washed with 2N hydrochloric acid (20 ml) to remove the triethylamine and 10% aq potassium carbonate solution to remove excess fluoroacetyl chloride. The organic layer was separated dried over magnesium sulphate and concentrated in high vacuum to 2-bromo-N-(2,3-dihydro-benzo-[1,4]dioxinyl-5-ylmethyl)-N-(2-phenoxyphenyl) acetamide, 637 mg, 1.40 mmole, 93%.

$^1$H NMR CDCl$_3$. 300 MHz, δ 3.77 (2H, dd, CH$_2$Br), 3.85-4.2 (4H, m, CH$_2$O×2), 4.75, and 5.15 (1H, d, together CH$_2$N), 6.65-7.4 (12H, m, ArH).

$^{13}$C NMR CDCl$_3$ 75 MHz, δ 27.77, 46.08, 63.95, 64.02, 116.68, 119.39, 120.66, 122.97, 123.00, 124.78, 124.28, 124.70, 129.50, 129.90, 130.40, 131.00 141.98, 143.16, 153.58, 155.50, 166.53.

Example 4

Synthesis of the Direct Labelling Precursor for In Vivo Imaging Agent 4

Example 4(i)

N-(2,2,-Dimethyl-2,3-dihydrobenzofuran-7-ylmethyl)-N-(2-phenoxy phenyl)amine

A mixture of 2-phenoxy-phenylamine (350 mg, 1.89 mmol) and 2,2-dimethyl-2,3-dihydro-1-benzofuran-7-carbaldehyde (500 mg, 2.83 mmol) was heated at 90° C. for 2 h under nitrogen. The reaction was cooled to 0° C. and MeOH (4 mL) was added, followed by NaBH$_4$ (216 mg, 5.70 mmol) in portions over 20 min. The mixture was stirred at room temperature for 24 h. Formic acid (0.4 mL was added and the mixture stirred for 15 min. The solvents were removed in vacuo, the residue quenched with saturated aqueous NaHCO$_3$ (50 mL), extracted with DCM (2×30 mL), dried over MgSO$_4$, filtered and solvents removed in vacuo. The crude material was purified by silica gel chromatography eluting with petroleum spirit (A) and ethyl acetate (B) (5-10% B, 80 g, 3 CV, 60 mL/min) to afford 560 mg (86%) of N-(2,2,-Dimethyl-2,3-dihydrobenzofuran-7-ylmethyl)-N-(2-phenoxy phenyl) amine as a colourless oil.

$^1$H NMR (300 MHz, CDCl$_3$) δ 1.43 (6H, s, C(C$\underline{H}_3$)$_2$), 2.98 (2H, s, ArC$\underline{H}_2$), 4.32 (2H, s, NC$\underline{H}_2$), 4.79 (1H, s, N$\underline{H}$), 6.60-7.10 (10H, m, ArH), 7.30 (2H, m, ArH).

Example 4(ii)

2-Bromo-N-(2,2,-Dimethyl-2,3-dihydrobenzofuran-7-ylmethyl)-N-(2-phenoxy phenyl)acetamide To a solution of N-(2,2,-Dimethyl-2,3-dihydrobenzofuran-7-ylmethyl)-N-(2-phenoxy phenyl)amine (0.20 g, 0.58 mmol) dissolved in DCM (2 mL) was added triethylamine (0.24 g, 2.32 mmol, 0.32 mL). The reaction was cooled to 0° C. and bromoacetyl chloride (0.18 g, 1.16 mmol, 0.10 mL) was added. The mixture was stirred at room temperature for 2 h. LC-MS indicated starting material and product (1:1). Further triethylamine (0.24 g, 2.32 mmol, 0.32 mL) and bromoacetyl chloride (0.18 g, 1.16 mmol, 0.10 mL) were added and stirred at room temperature for 2 h. The solvents were removed in vacuo, the residue quenched with water (10 mL), extracted with DCM (2×20 mL), dried over MgSO$_4$, filtered and solvents removed in vacuo. The crude material was purified by silica gel chromatography eluting with petroleum spirit (A) and EtOAc (B) (30% B, 80 g, 2.5 CV, 60 mL/min). The impure product was further purified by silica gel chromatography eluting with DCM (A) and EtOAc (B) (1-5% B, 80 g, 5 CV, 60 mL/min) to afford 170 mg (63%) of 2-Bromo-N-(2,2,-Dimethyl-2,3-dihydrobenzofuran-7-ylmethyl)-N-(2-phenoxy phenyl)acetamide as a colourless oil.

$^1$H NMR (300 MHz, CDCl$_3$) δ 1.14 (3H, s, C$\underline{H}_3$), 1.31 (3H, s, C$\underline{H}_3$), 2.83 (1H, d, J=15 Hz, ArC$\underline{H}$), 2.90 (1H, d, J=15 Hz, ArCH), 3.74 (1H, d, J=11 Hz, BrCH), 3.80 (1H, d, J=11 Hz, BrCH), 4.59 (1H, d, J=14 Hz, NCH), 5.22 (1H, d, J=14 Hz, NCH), 6.65-7.40 (12H, m, ArH)

LC-MS: m/z calcd for $C_{25}H_{24}BrNO_3$ 466.4. found, 467.9 (M+H)+

Example 5

Radio Fluorination of the Precursor Compounds of Examples 1-4 to Obtain In Vivo Imaging Agents 1-4

5(i) Drying [$^{18}$F] fluoride

To $^{18}$F-fluoride supplied in 15 μl water, a further 200 μl water was added, and the fluoride drawn into a COO vessel. In the presence of Kryptofix (2 mg, 5.3×10-6 moles), dissolved in 0.5 ml acetonitrile and 0.1M potassium hydrogen carbonate solution (50 μl, 5×10-6 moles), the $^{18}$F-fluoride was dried at 110° C./30 minutes under a flow of nitrogen (0.3 L/min for ~20 minutes followed by 0.1 L/min when the long tap was opened. The flow was turned up to 0.5 L/min when the risk of splashing was no longer (for ~10 min) and then cooled to room temperature.

5(ii) Radiofluorination

To the dry residue obtained in step 5(i) was added 0.7 mg of the selected precursor compound in 1 ml acetonitrile and the reaction heated in a sealed system at 100° C./10 minutes. After cooling, the reaction mixture was transferred to an N46 vial and the COO vial rinsed with 1.5 ml water. The washings were transferred to same glass vial. The prep (whose total volume was ~2.5 mL) was drawn onto the prep HPLC and the HPLC cut diluted in ~15 ml water prior to loading onto a Sep-Pak tC18 light (pre-conditioned with 2.5 ml ethanol and 5 ml water). The Sep-Pak was then eluted with 0.5 ml ethanol (collected into a P6 vial) followed by 4.6 ml Dulbecco's phosphate buffered saline collected into the same P6 vial. The RCP was measured by HPLC.

Example 6

Synthesis of a Non-Radioactive Standard for In Vivo Imaging Agent 1

Example 6(i)

N-(2,3-Dihydrobenxofuran-7-ylmethyl)-2-fluoro-N-(2-phenoxyphenyl)acetamide

N-(2,3-Dihydro-benzofuran-7-ylmethyl)-N-(2-phenoxyphenyl)-amine (0.5 g, 1.78 mmol) in DCM (20 ml) was treated with fluoroacetyl chloride (199 mg, 1.96 mmol) and TEA (199 mg, 1.96 mmol) at 0° C. for 1 h. The reaction was then diluted with DCM (50 ml) and washed with 2N hydrochloric acid (20 ml) to remove the TEA and 10% aq potassium carbonate to remove fluoroacetyl chloride. The organic layer separated dried over magnesium sulphate and concentrated in high vacuum to give N-(2,3-Dihydrobenxofuran-7-ylmethyl)-2-fluoro-N-(2-phenoxyphenyl)acetamide 455 mg, 1.61 mmole, 91%.

$^1$H NMR in CDCl$_3$, 300 mHz, δ 2.9-3.13 (2H, m, CH$_2$Ph), 4.22, and 4.38 (1H, q, together CH$_2$O) 4.7 and 4.9 (1H, q, together CH$_2$F), 4.8 and 5.1 (1H, d, together CH$_2$N), 6.63-7.5 (12H, m, ArH).

$^{13}$C NMR in CDCl$_3$, 75 MHz, δ 26.73, 43, 31, 68.03, 77.00, 114.00, 115.00 116.39, 117.32, 120.23, 121.34, 124.00, 126.36, 126.94, 127.45, 150.84, 152.58, 155.76, 164.11, 164.38.

Example 7

Synthesis of a Non-Radioactive Standard for In Vivo Imaging Agent 2

Example 7(i)

N-(benzo[1,3]-dioxol-4-ylmethyl)-2-Fluoro-N-(2-phenyloxy-phenyl)acetamide

To a solution of N-(benzo[1,3]dioxol-4-ylmethyl)-N-(2-phenyloxy-phenyl)amine (0.16 g, 0.50 mmol) dissolved in DCM (2 mL) was added TEA (0.20 g, 2.00 mmol, 0.28 mL).

The reaction was cooled to 0° C. and fluoroacetyl chloride (0.10 g, 1.00 mmol, 0.07 mL) was added. The mixture was stirred at room temperature for 1 h. The solvents were removed in vacuo, the residue quenched with water (10 mL), extracted with DCM (2×20 mL), dried over MgSO$_4$, filtered and solvents removed in vacuo. The crude material was purified by silica gel chromatography eluting with DCM (A) and MeOH (B) (1-5% B, 80 g, 4.0 CV, 60 mL/min) to afford 160 mg (84%) of N-(benzo[1,3]dioxol-4-ylmethyl)-2-Fluoro-N-(2-phenyloxy-phenyl)acetamide as a yellow oil. The structure was confirmed by $^1$H NMR (300 MHz, CDCl$_3$) δ 4.67 (1H, d, J=2 Hz, FCH), 4.83 (1H, d, J=2 Hz, FCH), 4.74 (1H, d, J=14 Hz, ArCH), 5.12 (1H, d, J=14 Hz, ArCH), 5.63 (1H, d, J=1 Hz, OCHO), 5.79 (1H, d, J=1 Hz, OCHO), 6.66-6.88 (6H, m, ArH), 6.96-7.06 (2H, m, ArH), 7.12-7.38 (4H, m, ArH).

$^{19}$F NMR (282 MHz, CDCl$_3$) δ −226.8, −227.0, −227.2.

LC-MS: m/z calcd for C$_{22}$H$_{18}$FNO$_4$ 379.4. found, 380.1 (M+H)+.

Example 8

Synthesis of a Non-Radioactive Standard for In Vivo Imaging Agent 3

Example 8(i)

2-fluoro-5 N-(2,3-Dihydro-benzo-[1,4]dioxinyl-5-ylmethyl)-N-(2-phenoxyphenyl)acetamide N-(2,3-Dihydro-benzo[1,4]-5-ylmethyl)-N-(2-phenoxyphenyl)-amine (0.5 g, 1.5 mmol) in DCM (20 ml) was treated with fluoroacetyl chloride (168 mg, 1.65 mmol) and TEA (168 mg, 1.65 mmol) at 0° C. for 1 h. The reaction was then diluted with DCM (50 ml) and washed with 2N hydrochloric acid (20 ml) and 10% aq potassium carbonate solution. The organic layer was separated dried over magnesium sulphate and concentrated in high vacuum to a gum. The gum was then chromatographed on 120 g silica column in a gradient of 15-40% ethyl acetate in petrol. The major fractions was collected to give 2-fluoro-N-(2,3-Dihydro-benzo-[1,4]dioxinyl-5-ylmethyl)-N-(2-phenoxyphenyl)acetamide (0.538 g, 1.43 mmole, 95%.)

$^1$H NMR in CDCl$_3$, 300 MHz, δ 3.8-4.1 (4H, M, CH$_2$O×2), 4.65, and 4.81 (1H, d, d, together, CH$_2$F), 4.8, and 5.1 (1H, d, d, together CH$_2$N), 6.6-7.4, (12H m, ArH).

$^{13}$C NMR in CDCl$_3$, 75 MHz, δ 45.2, 63.72, 63.83, 77.41, 79.75, 116.58, 119.16, 120.41, 122.98, 123.00, 124.16, 124.30, 129.00, 129.74, 130.00, 141.91, 143.05, 153.71, 155.23, 166.49, 166.75.

Example 9

Synthesis of a Non-Radioactive Standard for In Vivo Imaging Agent 4

Example 9(i)

—N-(2,2,-Dimethyl-2,3-dihydrobenzofuran-7-ylmethyl)-2-Fluoro-N-(2-phenoxy phenyl)acetamide To a solution of N-(2,2,-Dimethyl-2,3-dihydrobenzofuran-7-ylmethyl)-N-(2-phenoxy phenyl)amine (0.20 g, 0.58 mmol) dissolved in DCM (2 mL) was added TEA (0.24 g, 2.32 mmol, 0.32 mL). The reaction was cooled to 0° C. and fluoroacetyl chloride (0.11 g, 1.16 mmol, 0.08 mL) was added. The mixture was stirred at room temperature for 1 h. The solvents were removed in vacuo, the residue quenched with water (10 mL), extracted with DCM (2×20 mL), dried over MgSO$_4$, filtered and solvents removed in vacuo. The crude material was purified by silica gel chromatography eluting with DCM (A) and MeOH (B) (1% B, 80 g, 2 CV, 60 mL/min) to afford 170 mg (72%) of N-(2,2,-Dimethyl-2,3- dihydrobenzofuran-7-ylmethyl)-2-Fluoro-N-(2-phenoxy phenyl)acetamide as a pale yellow oil.

$^1$H NMR (300 MHz, CDCl$_3$) δ 1.12 (3H, s, CH$_3$), 1.30 (3H, s, CH$_3$), 2.83 (1H, d, J=15 Hz, ArCH), 2.90 (1H, d, J=15 Hz, ArCH), 4.58 (1H, d, J=14 Hz, NCH), 4.65 (1H, s, FCH), 4.81 (1H, s, FCH), 5.22 (1H, d, J=14 Hz, NCH), 6.65-7.40 (12H, m, ArH).

$^{19}$F NMR (282 MHz, CDCl$_3$) δ −226.6, −226.8, −227.0

LC-MS: m/z calcd for C$_{25}$H$_{24}$FNO$_3$ 405.5. found, 406.1 (M+H)+.

Example 10

In Vitro Potency Assay

Affinity for PBR was screened using a method adapted from Le Fur et al (Life Sci. 1983; USA 33: 449-57). The compounds tested were PBR06, and in vivo imaging agents 1-4.

Each test compound (dissolved in 50 mM Tris-HCl, pH 7.4, 10 mM MgCl$_2$ containing 1% DMSO) competed for binding to Wistar rat heart PBR against 0.3 nM [$^3$H] PK-11195. The reaction was carried out in 50 mM Tris-HCl, pH 7.4 10 mM MgCl$_2$ for 15 minutes at 25° C.

Each test compound was screened at 6 different concentrations over a 300-fold range of concentrations around the estimated K$_i$. The K$_i$ values for PBR06 and in vivo imaging agents 1-4 were found to be 0.28 nM, 0.31 nM 2.03 nM, 1.14 nM and 2.66 nM, respectively.

Example 11

In Vivo Biodistribution Method

PBR06 (synthesised according to Briard et al J Med Chem 2009; 52: 688-699) and in vivo imaging agents 1-3 were tested in an in vivo biodistribution model and their respective biodistributions compared.

Adult male Wistar rats (200-300 g) were injected with 1-3 MBq of test compound via the lateral tail vein. At 2, 10, 30 or 60 min (n=3) after injection, rats were euthanised and tissues or fluids were sampled for radioactive measurement on a gamma counter.

Figure 1:
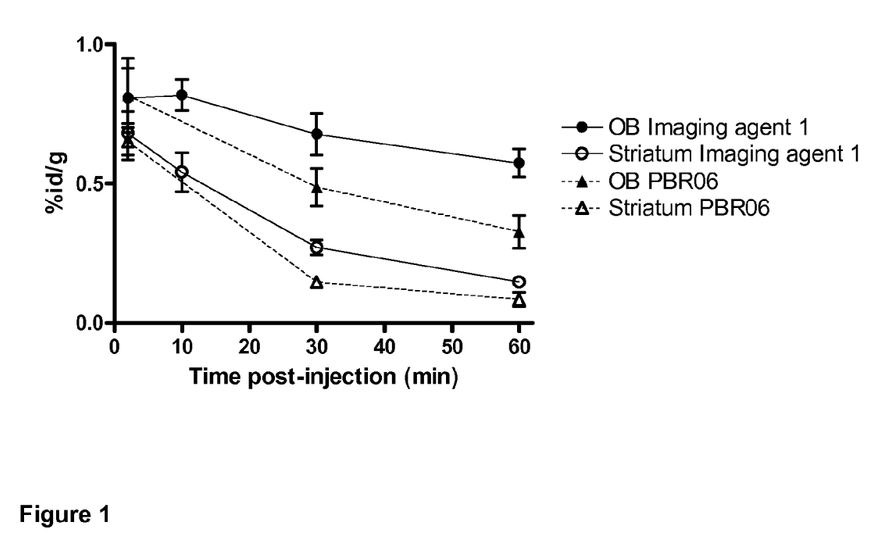
FIG. 1 shows the OB:striatum uptake of in vivo imaging agent 1 compared with PBR06.
Figure 2:
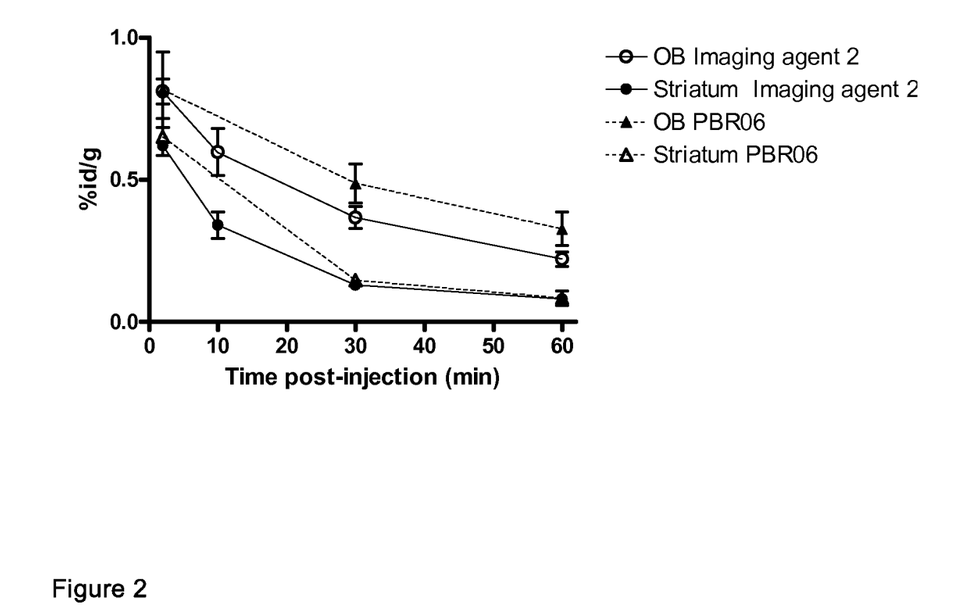
FIG. 2 shows the OB:striatum uptake of in vivo imaging agent 2 compared with PBR06.
Figure 3:
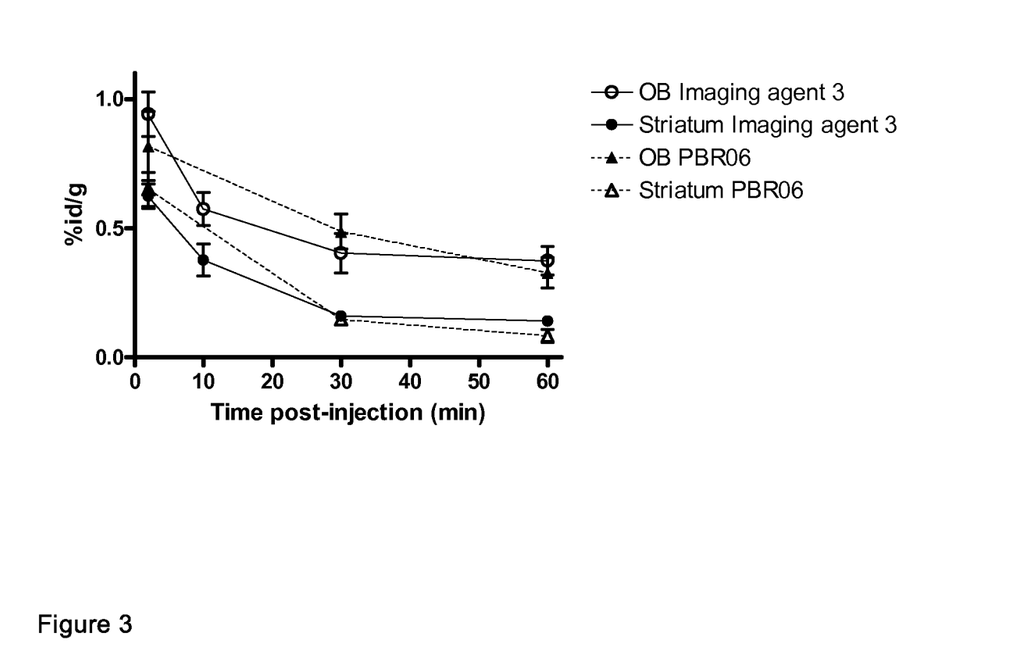
FIG. 3 shows the OB:striatum uptake of in vivo imaging agent 3 compared with PBR06.

FIGS. 1-3 illustrate the ratio of uptake of PBR06 and in vivo imaging agents 1-3, respectively, in OB compared to uptake in the striatum.

Example 12

Metabolism Assay

Brain tissue samples were collected from adult male Wistar rats (200-300 g) at 60 minutes after injection of test in vivo imaging agent. These samples were then processed via solvent extraction (see below) to extract the $^{18}$F-labelled parent along with any $^{18}$F-labelled metabolites, before introduction to the HPLC.

Brain (minus cerebellum +medulla pons) was homogenized with 10 mls of ice-cold Acetonitrile (5000 rpm for 5 mins) to extract all the $^{18}$F-labelled species. The resulting supernatant was then evaporated to dryness (rotary evaporation at 40° C.), concentrated in 2.5 mls of mobile phase, filtered and 1 ml was injected onto the HPLC.

The HPLC set up for $^{18}$F analysis was connected to a dual BGO radio & UV detector. A μBondapak C18 prep column was used having dimensions 7.8×300 mm; 10 μm; 125 Å. An isocratic elution system was used using between 30-40% water and between 60-70% acetonitrile. The flow rate was 3 ml/min. The aqueous to organic phase ratio was varied for each test in vivo imaging agent to obtain a parent peak at retention time at or around 10 min±2 min.

At 60 minutes post-injection the percentage of radioactivity in the brain representing intact test compound was 90%, 93% 92%, and 82%, respectively, for PBR06, and in vivo imaging agents 1-3.

What is claimed is:

1. An in vivo imaging agent of Formula I:

(I)

wherein:
A$^1$ is —CR$^1$R$^2$—(CH$_2$)$_n$— wherein R$^1$ and R$^2$ are independently selected from hydrogen, fluoro, or C$_{1-3}$ alkyl, and n is 0, 1 or 2;
A$^2$ is —CH$_2$—, —O— or —O—CH$_2$—; or,
-A$^1$-A$^2$- is —CH=CH—.

2. The in vivo imaging agent as defined in claim 1 wherein A$^1$ is —CR$^1$R$^2$—(CH$_2$)$_n$—.

3. The in vivo imaging agent as defined in claim 2 wherein A$^1$ is —(CH$_2$)$_m$— wherein m is 1, 2 or 3.

4. The in vivo imaging agent as defined in claim 3 wherein m is 1 or 2.

5. The in vivo imaging agent as defined in claim 1 wherein A$^2$ is —CH$_2$— or —O—.

6. A radiopharmaceutical composition comprising the in vivo imaging agent as defined in claim 1 together with a biocompatible carrier in a form suitable for mammalian administration.

7. An in vivo imaging method for determining the distribution and/or the extent of PBR expression in a subject comprising:
   wherein the said subject to whom the in vivo imaging agent as defined in claim 1 has been pre-administered;
   (ii) allowing said in vivo imaging agent to bind to PBR in said subject;
   (iii) detecting by an in vivo imaging procedure signals emitted by the $^{18}$F of said in vivo imaging agent;
   (iv) generating an image representative of the location and/or amount of said signals; and,
   (v) determining the distribution and extent of PBR expression in said subject wherein said expression is directly correlated with said signals emitted by said in vivo imaging agent.

8. The in vivo imaging method as defined in claim 7 which is carried out repeatedly during the course of a treatment regimen for said subject, said regimen comprising administration of a drug to combat a PBR condition.

9. The in vivo imaging method as defined in claim 7 which comprises the further step (vi) of attributing the distribution and extent of PBR expression to diagnose whether said subject is suffering from a PBR condition.

* * * * *